US008815265B2

(12) United States Patent
Ptchelintsev et al.

(10) Patent No.: US 8,815,265 B2
(45) Date of Patent: *Aug. 26, 2014

(54) COSMETIC USE OF N-SUBSTITUTED SULFONYLOXYBENZYLAMINES AND RELATED COMPOUNDS

(75) Inventors: Dmitri S. Ptchelintsev, Jersey City, NJ (US); John W. Lyga, Basking Ridge, NJ (US); Russell Wyborski, Pine Island, NY (US); Qian Zheng, Morris Plains, NJ (US); Cheng S. Hwang, New Milford, NJ (US)

(73) Assignee: Avon Products, Inc., New York, NY (US)

( * ) Notice: Subject to any disclaimer, the term of this patent is extended or adjusted under 35 U.S.C. 154(b) by 285 days.

This patent is subject to a terminal disclaimer.

(21) Appl. No.: 12/826,864

(22) Filed: Jun. 30, 2010

(65) Prior Publication Data

US 2012/0004302 A1    Jan. 5, 2012

(51) Int. Cl.
*A61K 8/42* (2006.01)
*A61Q 19/08* (2006.01)
*A61K 8/46* (2006.01)

(52) U.S. Cl.
CPC ............... *A61K 8/466* (2013.01); *A61Q 19/08* (2013.01); *Y10S 514/828* (2013.01); *Y10S 514/848* (2013.01); *Y10S 514/827* (2013.01)
USPC ............... 424/401; 424/70.24; 424/78.03; 514/517; 514/828; 514/848; 514/827

(58) Field of Classification Search
CPC ............... A61K 8/466; A61Q 19/08
USPC ............ 424/401, 70.24, 78.03; 514/517, 828, 514/848, 827
See application file for complete search history.

(56) References Cited

U.S. PATENT DOCUMENTS

| 4,122,029 | A | 10/1978 | Gee et al. |
| 4,781,917 | A | 11/1988 | Luebbe et al. |
| 6,685,952 | B1 | 2/2004 | Ma et al. |
| 7,928,127 | B2 | 4/2011 | Lee et al. |
| 2005/0000531 | A1 | 1/2005 | Shi |
| 2007/0185038 | A1 | 8/2007 | Bissett et al. |
| 2008/0090855 | A1 | 4/2008 | Frank et al. |
| 2009/0068126 | A1 | 3/2009 | Soares Romeiro et al. |
| 2012/0003332 | A1* | 1/2012 | Zheng et al. .................. 424/725 |
| 2012/0165373 | A1* | 6/2012 | Khusial et al. ................ 514/331 |

FOREIGN PATENT DOCUMENTS

| WO | 2004/103334 A1 | 12/2004 |
| WO | 2006/091862 A2 | 8/2006 |
| WO | 2007/058990 A2 | 5/2007 |
| WO | 2008/124836 A2 | 10/2008 |
| WO | 2010/115491 A2 | 10/2010 |

OTHER PUBLICATIONS

Todd et al., "Volatile Silicone Fluids for Cosmetics", Cosmetics and Toiletries, vol. 91:27-32 (1976).
Uhlmann, et al., "Flavor encapsulation technologies: an overview including recent developments" Perfumer and Flavorist, 27, 52-61, 2002.
Sparks and Jacobs, "Selection of Coating and Microencapsulation Processes" in Controlled-Release Delivery Systems for Pesticides, Herbert B. Scher ed., Marcel Dekker, New York, N.Y., 1999, pp. 3-29.
J.M. Garcia-Antón 2006, "The Scientific Response to Different Types of Wrinkles," SÖFW-Journal 132(4):8-16.

* cited by examiner

*Primary Examiner* — Mina Haghighatian
(74) *Attorney, Agent, or Firm* — David M. Joyal; Joan M. McGillycuddy

(57) ABSTRACT

Cosmetic compositions comprising N-substituted sulfonyloxybenzylamines and methods of using such compositions to impart anti-aging benefits to the skin are disclosed. The N-substituted sulfonyloxybenzylamines are believed to have modulatory activity against one or more biochemical pathways implicated in skin aging.

19 Claims, No Drawings

COSMETIC USE OF N-SUBSTITUTED SULFONYLOXYBENZYLAMINES AND RELATED COMPOUNDS

FIELD OF INVENTION

The present invention relates generally to compositions for topical application to the skin which comprise N-substituted sulfonyloxybenzylamines and the use of such compositions to improve the aesthetic appearance of the skin.

BACKGROUND OF THE INVENTION

Collagen is the body's major structural protein and is composed of three protein chains wound together in a tight triple helix. This unique structure gives collagen a greater tensile strength than steel. Approximately 33 percent of the protein in the body is collagen. This protein supports tissues and organs and connects these structures to bones. In fact, bones are also composed of collagen combined with certain minerals such as calcium and phosphorus. Collagen plays a key role in providing the structural scaffolding surrounding cells that helps to support cell shape and differentiation, similar to how steel rods reinforce a concrete block. The mesh-like collagen network binds cells together and provides the supportive framework or environment in which cells develop and function, and tissues and bones heal.

Collagen is created by fibroblasts, which are specialized skin cells located in the dermis. Fibroblasts also produce other skin structural proteins such as elastin (a protein which gives the skin its ability to snap back) and glucosaminoglycans (GAGs). GAGs make up the ground substance that keeps the dermis hydrated. In order to signal or turn on the production of skin structural proteins, fibroblast cells have specially shaped receptors on their outside membranes that act as binding sites to which signal molecules with a matching shape can fit. When the receptors are bound by the correct combination of signal molecules (called fibroblast growth factors, or FGFs), the fibroblast begins the production of collagen. The stimulation of collagen gives the skin its strength, durability, and smooth, plump appearance.

The invention thus provides new compositions and methods for stimulating collagen production. It is a further object of the invention to improve the overall appearance of skin, including treating, reversing, and/or preventing signs of aging, such as skin wrinkles, by stimulating collagen production with cosmetic compositions comprising effective amounts of N-substituted sulfonyloxybenzylamines.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that N-substituted sulfonyloxybenzylamines are potent stimulators of collagen production and thus are beneficial agents against various signs of intrinsic aging and photo-aging of skin.

In one aspect of the invention, a method is provided for improving the aesthetic appearance of human skin comprising topically applying to an area of the skin in need thereof an effective amount of an N-substituted sulfonyloxybenzylamine or a cosmetically acceptable salt thereof in a cosmetically acceptable vehicle.

In another aspect of the invention, cosmetic compositions are provided for improving the aesthetic appearance of skin comprising, in a cosmetically acceptable vehicle, an effective amount of an N-substituted sulfonyloxybenzylamine having the structure of formula I:

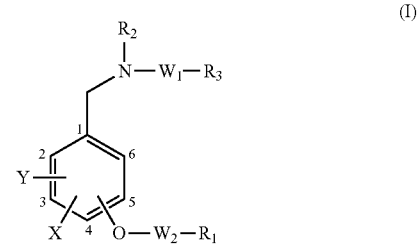

where $W_1$, $W_2$ are independently CO, $CO_2$, CONH, $SO_2$ or $PO_3$;

$R_1$, $R_2$ and $R_3$ are independently $C_{1-20}$ hydrocarbons, each independently selected from alkyl, cycloalkyl, haloalkyl, alkoxyalkyl, heteroalkyl, aryl, arylalkyl, alkylaryl, heteroarylalkyl, and alkylheteroaryl, and each being optionally substituted with C and/or 1-6 heteroatoms, selected from halogens, O, N, S, and with S optionally being oxidized;

X, Y each independently represent H or an optionally substituted alkyl, haloalkyl, alkoxy, amino, aminoalkyl, haloalkoxy, alkenyl, and where adjacent X, Y taken together can form a 5, 6, or 7 member ring;

$R_1$, $R_2$ and $R_3$ each may also be optionally substituted with, for example, amino, aminoalkyl, alkoxy, haloalkoxy, haloalkyl, alkyl, alkenyl, alkynyl, cycloalkyl, aryl, etc.

and wherein the —O—$W_2$—$R_1$ group is attached to the phenyl ring at the 2-, 3- or 4-position.

Also provided is a method of treating one or more signs of skin aging comprising topically applying to skin in need thereof an N-substituted sulfonyloxybenzylamine according to formula I in an amount effective to enhance collagen.

In another aspect of the invention, a method of treating, ameliorating, and/or preventing fine lines or wrinkles or sagging in human skin is provided, comprising topically applying to skin in need thereof, including applying directly to a wrinkle or fine line, a composition comprising a N-substituted sulfonyloxybenzylamine according to formula I in an amount effective to enhance collagen.

These and other aspects of the present invention will be better understood by reference to the following detailed description and accompanying figures.

DETAILED DESCRIPTION

All terms used herein are intended to have their ordinary meaning unless otherwise provided.

The present invention provides compositions for topical application which comprise and effective amount of N-substituted sulfonyloxybenzylamines or a related compound to treat, reverse, ameliorate and/or prevent signs of skin aging. Such signs of skin aging include without limitation, the following:

(a) treatment, reduction, and/or prevention of fine lines or wrinkles, (b) reduction of skin pore size, (c) improvement in skin thickness, plumpness, and/or tautness;

(d) improvement in skin suppleness and/or softness;

(e) improvement in skin tone, radiance, and/or clarity;

(f) improvement in procollagen and/or collagen production;

(g) improvement in maintenance and remodeling of elastin;

(h) improvement in skin texture and/or promotion of retexturization;

(i) improvement in skin barrier repair and/or function;

(j) improvement in appearance of skin contours;

(k) restoration of skin luster and/or brightness;

(l) replenishment of essential nutrients and/or constituents in the skin;

(m) decreased by aging and/or menopause;

(n) improvement in skin moisturization;

(o) increase in skin elasticity and/or resiliency;

(p) treatment, reduction, and/or prevention of skin sagging and/or (q) reduction of pigment spots.

In practice, the compositions of the invention are applied to skin in need of treatment. That is, skin which suffers from a deficiency or loss in any of the foregoing attributes or which would otherwise benefit from improvement in any of the foregoing skin attributes.

In certain preferred embodiments the compositions and methods of the invention are directed to the prevention, treatment, and/or amelioration of fine lines and/or wrinkles in the skin. In this case, the compositions are applied to skin in need of treatment, by which is meant skin having wrinkles and/or fine lines. Preferably, the compositions are applied directly to the fine lines and/or wrinkles. The compositions and The cosmetic compositions for treating a skin condition associated with loss of collagen and/or elastin fiber comprise, in a cosmetically acceptable vehicle, an amount of a N-substituted sulfonyloxybenzylamines effective to enhance collagen. These collagen enhancing agents may have the structure of formula (I):

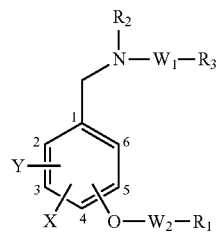

In formula (I), $W_1$ and $W_2$ are independently CO, $CO_2$, CONH, $SO_2$, or $PO_3$; $R_1$, $R_2$ and $R_3$ are independently alkyl, cycloalkyl, haloalkyl, alkoxyalkyl, arylaklyl or heteroalkyl, each which may be optionally substituted with C and/or 1-6 heteroatoms, selected from halogens, O, N, S, and with S optionally being oxidized; X, Y each independently represent H or are optionally substituted alkyl, haloalkyl, alkoxy, amino, aminoalkyl, haloalkoxy, alkenyl, and where adjacent X, Y taken together can form a 5, 6, or 7 member ring.

In one embodiment, $W_1$ and $W_2$ are $SO_2$, X and Y are H; $R_1$, $R_2$ each represent $C_1$-$C_8$ alkyl, preferably $C_1$-$C_4$ alkyl, and $R_3$ is an aliphatic alkyl, $C_1$-$C_8$ substituted or unsubstituted cycloalkyl, or an aromatic hydrocarbon radical, as exemplified by $C_6$ aromatic hydrocarbon radical which may be a substituted or unsubstituted aryl (e.g., phenyl). In other embodiments $R_1$, $R_2$, $R_3$ independently represent a lower alkyl group (e.g., methyl, ethyl, propyl, butyl, etc.), typically methyl or ethyl). In other embodiments, $R_1$, $R_2$ represent, independently at each occurrence aliphatic $C_1$-$C_8$ hydrocarbon radicals; including aliphatic $C_1$-$C_6$ hydrocarbon radicals, aliphatic $C_1$-$C_8$ hydrocarbon radicals, or an aliphatic $C_1$-$C_6$ hydrocarbon radicals, as exemplified by substituted or unsubstituted branched, straight chain or cyclic, alkyl, alkenyl (e.g., vinyl, allyl, etc.), and alkynyl moieties; $C_6$-$C_{20}$ aromatic hydrocarbon radicals, including $C_6$-$C_{12}$ aromatic hydrocarbon radicals, $C_6$-$C_{10}$ aromatic hydrocarbon radicals, or $C_6$ aromatic hydrocarbon radicals, as exemplified by substituted or unsubstituted aryl (e.g., phenyl), alkyl-aryl (e.g., benzyl), aryl-alkyl, and the like; or $C_1$-$C_{20}$ heteroaryl radicals including one or more heteroatoms selected from O, N, and S in the ring; including $C_1$-$C_{12}$ heteroaromatic radicals, $C_1$-$C_8$ heteroaromatic radicals, and $C_1$-$C_6$ heteroaromatic radicals, as exemplified by heteroaryl, alkyl-heteroaryl, heteroarylalkyl and the like.

$R_1$, $R_2$ and $R_3$ each may also be optionally substituted with, for example, amino, aminoalkyl, alkoxy, haloalkoxy, haloalkyl, halogen, amino, aminoalkyl, alkoxy, haloalkoxy, haloalkyl, alkyl, alkenyl, alkynyl, cycloalkyl, aryl, etc.

In some embodiments, $W_1$ is CONH, $W_2$ is $SO_2$, X and Y are H, $R_1$ is $C_1$-$C_8$ alkyl, $R_2$ is $C_1$-$C_8$ alkyl or aralkyl, and $R_3$ is alkyl, cycloalkyl, arylalkyl or heteroalkyl.

In other embodiments, $W_1$ represents a carbonyl group —(C=O)—, $W_2$ is $SO_2$, X and Y are H, $R_1$ is $C_1$-$C_8$ alkyl, $R_2$ is $C_1$-$C_8$ alkyl or arylalkyl, and $R_3$ is alkyl, cycloalkyl, arylalkyl or heteroalkyl.

Further, any nitrogen atom may be optionally oxidized to the N-oxide or can be quarternized, for example with lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides such as benzyl and phenethyl bromides, to name a few.

In one embodiment according to formula (I), $W_1$ and $W_2$ are $SO_2$, as shown in formula (Ia).

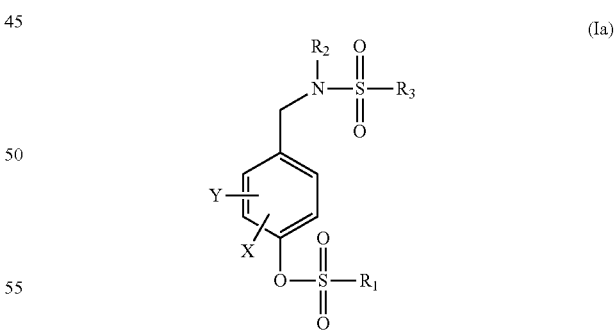

where X and Y are H, $R_1$ is an alkyl group, $R_2$ is i-butyl and $R_3$ is a phenyl group.

In another embodiment, $W_1$ is $SO_2$ and $W_2$ will be a group —CONH—, X and Y are H, $R_1$ is an alkyl group, $R_2$ is an alkyl group and $R_3$ is substituted phenyl group as shown in formula (Ib):

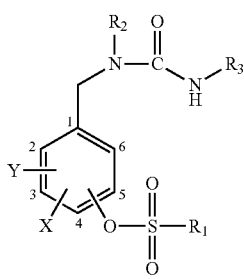

(Ib)

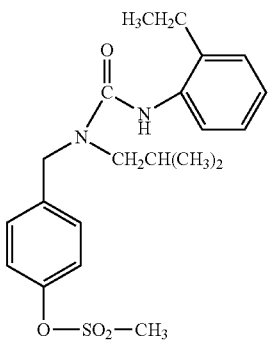

where the —OSO$_2$R$_1$ group is positioned on the phenyl ring at position 3- or 4-. Preferably R is a methyl group, R$_2$ is isobutyl and R$_3$ is a 2-ethyl phenyl group.

In a further embodiment, W$_1$ is a be a carbonyl group (—CO—), W$_2$ is SO$_2$, X and Y are H, R$_1$ is an alkyl group, R$_2$ is alkyl group and R$_3$ is an alkyl group or substituted phenyl group as shown in formula (Ic):

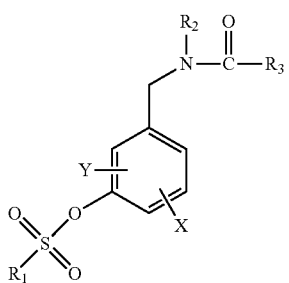

(Ic)

where R$_1$ is preferably methyl, R$_2$ is an alkyl group or an alkoxy group and R$_3$ is a substituted phenyl group.

In a particular embodiment, a cosmetic composition comprises, in a cosmetically acceptable vehicle, preferably a water-in-oil or oil-in-water emulsion, from about 0.0001% to about 90% by weight of a N-substituted sulfonyloxybenzylamine having the structure:

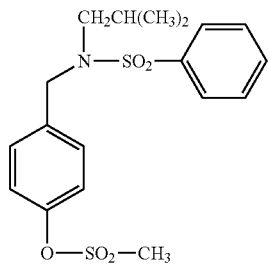

or a cosmetically acceptable salt thereof.

In another particular embodiment, a cosmetic composition comprises, in a cosmetically acceptable vehicle, preferably a water-in-oil or oil-in-water emulsion, from about 0.0001% to about 90% by weight of a N-substituted sulfonyloxybenzylamine having the structure:

or a cosmetically acceptable salt thereof.

The invention embraces the use of cosmetically or pharmaceutically acceptable (e.g., non-toxic and/or non-irritating) salts. Examples of the salts of the compounds in the present invention include salts with alkali metals such as sodium and potassium; salts with alkaline-earth metals such as calcium and magnesium; salts with amines such as monoethanolamine; salts with inorganic acids such as hydrochloric acid and sulfuric acid; and salts with organic acids such as citric acid and acetic acid. Special mention may be made of hydrochloride salts.

The cosmetic compositions according to the invention can be formulated in a variety of forms for topical application and will comprise from about 0.00001% to about 90% by weight of one or more compounds according to formula (I), and preferably will comprise from about 0.001% to about 25% by weight, and more preferably from about 0.001% to about 1% by weight. The compositions will comprise an effective amount of the N-substituted sulfonyloxybenzylamine compounds according to formula (I), by which is meant an amount sufficient to enhance collagen in s given area of skin when topically applied thereto.

The composition may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The compositions can include a cosmetically acceptable vehicle. Such vehicles may take the form of any known in the art suitable for application to skin and may include, but are not limited to, water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion preferably has one or more organic compounds, including emollients; humectants (such as propylene glycol and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99ATM are also contemplated to be suitable. Various commercially available $C_{16}$ isoparaffins, such as isohexadecane (having the tradename Permethyl®) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isodecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers included emulsifying waxes, emulsifying polyhydric alcohols, polyether polyols, polyethers, mono- or di-ester of polyols, ethylene glycol monostearates, glycerin mono-stearates, glycerin di-stearates, silicone-containing emulsifiers, soya sterols, fatty alcohols such as cetyl alcohol, fatty acids such as stearic acid, fatty acid salts, and mixtures thereof. The preferred emulsifiers include soya sterol, cetyl alcohol, stearic acid, emulsifying wax, and mixtures thereof. Other specific emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference.

These emulsifiers typically will be present in the composition in an amount from about 0.001% to about 10% by weight, in particular in an amount from about 0.01% to about 5% by weight, and more preferably, below 1% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)m- and/or —(PO)n-groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), and dimethicone PEG-10/15 crosspolymer (trade name KSG-210, Shin-Etsu).

The water-in-silicone emulsifiers typically will be present in the composition in an amount from about 0.001% to about 10% by weight, in particular in an amount from about 0.01% to about 5% by weight, and more preferably, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

The compositions may include liposomes. The liposomes may comprise other additives or substances and/or may be modified to more specifically reach or remain at a site following administration.

Additionally, the compositions may incorporate encapsulation and/or microencapsulation technology. As is well known in the art, encapsulating materials can be selected which will release the composition upon exposure to moisture, pH change, temperature change, solubility change, or mechanical shear or rupture. Suitable encapsulating materials and methods of preparing encapsulated materials, such as spray drying, extrusion, coacervation, fluidized bed coating, liposome entrapment and others, are disclosed in, for example, U.S. Patent Application Publication No. 2005/0000531 to Shi; Uhlmann, et al., "Flavor encapsulation technologies: an overview including recent developments" Perfumer and Flavorist, 27, 52-61, 2002; and "Selection of Coating and Microencapsulation Processes" by Robert E. Sparks and Irwin Jacobs in Controlled-Release Delivery Systems for Pesticides, Herbert B. Scher ed., Marcel Dekker, New York, N.Y., 1999, pp. 3-29, the contents of which are hereby incorporated by reference.

The compositions incorporating encapsulation and/or microencapsulation technology may form nanoparticles. The term "nanoparticle" as used herein refers to a nanometer-sized particle, having a diameter of between about 1 nanometer and about 999 nanometers; the term "nanoparticles" as used herein refers to nanometer-sized particles, nanoclusters, clusters, particles, small particles, and nanostructured materials.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives, stabilizers, pharmaceutical agents, photostabilizing agents, sunscreens, and mixtures thereof. In addition to the foregoing, the cosmetic compositions of the invention may contain any other compound for the treatment of skin disorders.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions may include additional skin actives such as, but are not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, and advanced glycation end-product (AGE) inhibitors.

In a specific embodiment, the composition may comprise at least one additional botanical, such as, for example, a botanical extract, an essential oil, or the plant itself. Suitable botanicals include, without limitation, extracts from *Abies*

*pindrow, Acacia catechu, Aloe, Amorphophallus campanulatus, Anogeissus latifolia, Asmunda japonica, Azadirachta indica, Butea frondosa, Butea monosperma, Cedrus deodara, Chamomile, Emblica officinalis, Ficus benghalensis, Glycyrrhiza glabra, Humilus scandens, Ilex purpurea* Hassk, *Innula racemosa, Ligusticum chiangxiong, Ligusticum lucidum, Mallotus philippinensis, Melicope hayesil, Mimusops elengi, Morinda citrifolia, Moringa oleifera, Naringi crenulata, Nerium indicum, Piper betel, Pouzolzia petandra, Psoralea corylifolia, Rhinacanthus nasutus, Sapindus rarek, Sesbania grandiflora, Stenoloma chusana, Terminalia bellerica,* tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea Frondosa* extract); phytol, thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles Examples include isopropyl myristate, petrolatum, isopropyl lanolate, silicones (e.g., methicone, dimethicone), oils, mineral oils, fatty acid esters, or any mixtures thereof. The emollient may be preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

It is preferred that the composition be essentially free of components having a strong oxidizing potential, including for example, organic or inorganic peroxides. By "essentially free of" these components is meant that the amounts present are insufficient to have a measurable impact on the collagen enhancing activity of the N-substituted sulfonyloxybenzylamine. In some embodiments, this will be, on a molar basis in relation to the amount of N-substituted sulfonyloxybenzylamine, less than 1%.

In one embodiment, the composition of the invention comprising an N-substituted sulfonyloxybenzylamine may have a pH between about 1 and about 8. In certain embodiments, the pH of the composition will be acidic, i.e., less than 7.0, and preferably will be between about 2 and about 7, more preferably between about 3.5 and about 5.5.

The invention provides a method for treating aging skin by topically applying a composition comprising a N-substituted sulfonyloxybenzylamine, preferably in a cosmetically acceptable vehicle, over the affected area for a period of time sufficient to reduce, ameliorate, reverse or prevent dermatological signs of aging. This method is particularly useful for treating signs of skin photoaging and intrinsic aging.

Generally, the improvement in the condition and/or aesthetic appearance is selected from the group consisting of: reducing dermatological signs of chronological aging, photoaging, hormonal aging, and/or actinic aging; preventing and/ or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

Without wishing to be bound by any particular theory, it is believed that the compositions of the present invention enhance and improve the aesthetic appearance of skin by stimulation of collagen and/or by improving the cell-to-cell adhesion between keratinocytes through the stimulation of Desmogleins.

The composition will typically be applied to the skin one, two, or three times daily for as long as is necessary to achieve desired anti-aging results. The treatment regiment may comprise daily application for at least one week, at least two weeks, at least four weeks, at least eight weeks, or at least twelve weeks. Chronic treatment regimens are also contemplated.

The N-substituted sulfonyloxybenzylamine active component is topically applied to an "individual in need thereof," by which is meant an individual that stands to benefits from reducing visible signs of skin damage or aging. In a specific embodiment, the N-substituted sulfonyloxybenzylamine component is provided in a pharmaceutically, physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating fine lines and wrinkles comprise topically applying the inventive N-substituted sulfonyloxybenzylamine compositions to the skin of an individual in need thereof, e.g., topically application directly to the fine line and/or wrinkle in an amount and for a time sufficient to reduce the severity of the fine lines and/or wrinkles or to prevent or inhibit the formation of new fine lines and/or wrinkles. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of wrinkles on the skin of the hands, arms, legs, neck, chest, and face, including the forehead, It is also contemplated that the compositions of the invention will be useful for treating thin skin by topically applying the composition to thin skin of an individual in need thereof. "Thin skin" is intended to include skin that is thinned due to chronological aging, menopause, or photo-damage. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in patients that have not manifested signs of skin aging, most commonly in individuals under 25 years of age. The method may also reverse or treat signs of aging once manifested as is common in patients over 25 years of age.

The following examples are meant to demonstrate certain aspects of the invention in a non-limiting fashion.

EXAMPLES

Example 1

Collagen Assay

Human dermal fibroblasts (Cascade Biologics, Portland, Oreg.) were plated at 10,000 cells/well in 96-well culture plates in supplemented medium (DMEM, 10% Fetal Bovine Serum, 1% Penicillin/Streptomycin and 1% L-Glutamine) overnight in humidified atmosphere of 10% $CO_2$ at 37° C. The next day, the medium was replaced with fresh medium (DMEM, 1% Penicillin/Streptomycin and 1% L-Glutamine) and the compounds dissolved in DMSO were added to the wells in triplicate at a concentration of 0.0005%. DMSO solution was used a control. Following 48-hour incubation, the plates were removed from the incubator and the medium from each well was collected for the procollagen assay.

Collagen production was measured using procollagen type I C-peptide (PIP) EIA kit (Takara Bio, Inc., Japan). Briefly, the conditioned medium was diluted 1:10 in Sample Diluent. 20 µl of diluted conditioned medium and 100 µl of antibody-POD conjugate solution were added to the wells of the Takara ELISA plate. The ELISA plate was incubated at 37° C. for 3 hours before the wells were washed four times with 400 µl of 1×PBS. At the end of wash, 100 µl of substrate solution (supplied with kit) was added to the wells and incubated at room temperature for 15 minutes. The reaction was stopped by adding 100 µl of 1N sulfuric acid to the wells. The absorbance was measured on a spectrophotometer at 450 nm wavelength. The amount of procollagen peptide in the conditioned medium was calculated from the standard curve. The stimulation of collagen production was shown as an increase in collagen over the control.

The results of compounds tested in the collagen assay are illustrated in Table 1:

TABLE 1

Analogs active at stimulating collagen synthesis

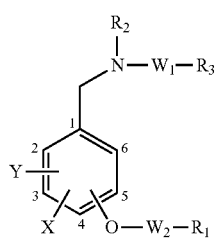

| Compound Number | Position | $R_1$ | $R_2$ | $R_3$ | Stimulation of collagen production* |
|---|---|---|---|---|---|
| 1 | 4 | $CH_3$ | i-butyl | $SO_2$Phenyl | ++++ |
| 2 | 4 | $CH_3$ | i-butyl | CONH(2-Et)Ph | ++++ |
| 3 | 3 | $CH_2CH_3$ | $CH_2$-2-furanyl | CONH-c-hexyl | +++ |
| 4 | 3 | $CH_2CH_3$ | s-butyl | CO(4-$OCH_3$)Ph | +++ |
| 5 | 3 | $CH_3$ | Methoxyethyl | CO(4-Cl)Ph | +++ |
| 6 | 3 | $CH_3$ | i-butyl | CObutyl | +++ |
| 7 | 3 | $CH(CH_3)_2$ | i-butyl | CO-i-butyl | ++++ |
| 8 | 4 | $CH_2CH_3$ | i-butyl | CO-c-propyl | ++++ |
| 9 | 3 | $CH_2CH_3$ | i-propyl | CONH-t-butyl | +++ |
| 10 | 3 | $CH(CH_3)_2$ | i-butyl | CO-c-butyl | +++ |

"+++" 51-80% increase in collagen over control;
"++++" >81% increase in collagen over control All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for improving the aesthetic appearance of human skin comprising topically applying to an area of the skin in need thereof an effective amount of an N-substituted sulfonyloxybenzylamine or a cosmetically acceptable salt thereof in a cosmetically acceptable vehicle.

2. The method according to claim 1 wherein said N-substituted sulfonyloxybenzylamine has the structure of formula I:

where:
$W_1$ and $W_2$ are independently CO, $CO_2$, CONH, $SO_2$ or $PO_3$;
$R_1$, $R_2$ and $R_3$ are independently $C_{1-20}$ hydrocarbons, each independently selected from alkyl, cycloalkyl, haloalkyl, alkoxyalkyl, heteroalkyl, heteroaryl, aryl, arylalkyl, alkylaryl, heteroaryl, heteroarylalkyl, and alkylheteroaryl, each being optionally substituted with C and/or 1-6 heteroatoms, including halogen, O, N and S;
X, Y each independently represent H or an optionally substituted alkyl, haloalkyl, alkoxy, amino, aminoalkyl, haloalkoxy, alkenyl, and where adjacent X, Y taken together can form a 5, 6, or 7 member ring;
and wherein the —O—$W_2$—$R_1$ group is attached to the phenyl ring at the 3- or 4-position.

3. The method according to claim 2, where $R_1$ is a $C_{1-4}$ alkyl group.

4. The method according to claim 3, where $R_1$ is —$CH_3$ or —$CH_2CH_3$.

5. The method according to claim 2, where $R_2$ is selected from the group consisting of i-butyl, sec-butyl, methoxyethyl and $CH_2$-2-furanyl.

6. The method according to claim 5, where $R_2$ is a group i-butyl.

7. The method according to claim 2, where $W_1$ and $W_2$ are independently selected from the group consisting of CO, CONH, and $SO_2$.

8. The method according to claim 7, where $W_1$ is a group —$SO_2$ or a group —CONH, and $W_2$ is a group —$SO_2$.

9. The method according to claim 2, where $R_3$ is alkyl, cycloalkyl or aryl.

10. The method according to claim 9, where $R_3$ is phenyl.

11. The method according to claim 1, wherein said aesthetic improvement of said human skin is selected from the group consisting of:
(a) treatment and/or reduction of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by menopause;
(n) improvement in skin moisturization;
(o) increase in skin elasticity and/or resiliency;
(p) treatment and/or reduction of skin sagging; and
(q) reduction of pigment spots.

12. The method according to claim 11, wherein said aesthetic improvement of said skin is the treatment and/or reduction of: fine lines and/or wrinkles, skin sagging, loss of elasticity and mottled skin appearance.

13. The method according to claim 2, wherein said N-substituted sulfonyloxybenzylamine has the structure:

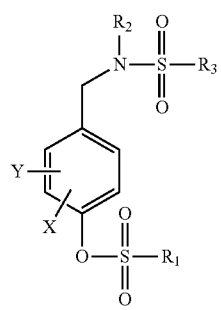

or a cosmetically acceptable salt thereof,
where:
X and Y are H;
$R_1$ is a $C_{1-8}$ alkyl group, a phenyl group or benzyl group, each being optionally substituted with C and/or 1-6 heteroatoms, including halogen, O, N and S;
$R_2$ is alkyl, aryl, alkylaryl or heteroaryl, each being optionally substituted with C and/or 1-6 heteroatoms, including halogen, O, N and S; and
$R_3$ is alkyl or aryl, each being optionally substituted with C and/or 1-6 heteroatoms, including halogen, O, N and S.

14. The method according to claim 2, wherein said N-substituted sulfonyloxybenzylamine has the structure:

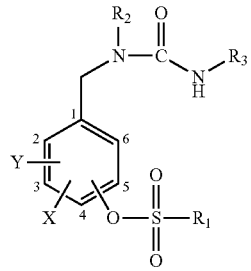

or a cosmetically acceptable salt thereof,
where
X and Y are H;
$R_1$ is a $C_{1-8}$ alkyl group, a phenyl group or benzyl group, each being optionally substituted with C and/or 1-6 heteroatoms, including halogen, O, N and S;
$R_2$ is alkyl, aryl, alkylaryl or heteroaryl each being optionally substituted with C and/or 1-6 heteroatoms, including halogen, O, N and S; and
$R_3$ is alkyl or aryl each being optionally substituted with C and/or 1-6 heteroatoms, including halogen, O, N and S; and
wherein said —O—$SO_2$—$R_1$ group is attached to the phenyl ring at the 3- or 4-position.

15. The method according to claim 2, wherein said N-substituted sulfonyloxybenzylamine has the structure:

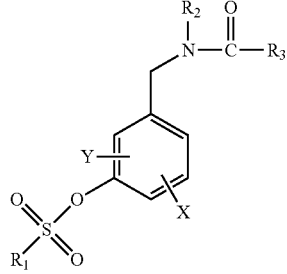

where:
X and Y are H;
$R_1$ is a $C_{1-8}$ alkyl group, a phenyl group or benzyl group, each being optionally substituted with C and/or 1-6 heteroatoms, including halogen, O, N and S;
$R_2$ is alkyl, aryl, alkylaryl or heteroaryl, each being optionally substituted with C and/or 1-6 heteroatoms, including halogen, O, N and S; and
$R_3$ is alkyl or aryl, each being optionally substituted with C and/or 1-6 heteroatoms, including halogen, O, N and S.

16. A method for treating wrinkles and/or fine lines comprising topically applying to said wrinkle and/or fine line on the skin of an individual in need thereof an effective amount of a N-substituted sulfonyloxybenzylamine or a cosmetically acceptable salt thereof in a cosmetically acceptable vehicle for a time sufficient to reduce the severity of said wrinkles or fine lines.

17. The method according to claim 16, wherein said N-substituted sulfonyloxybenzylamine or a cosmetically acceptable salt thereof is applied to said skin at least once daily for a period of at least four weeks.

18. The method according to claim 15, wherein said N-substituted sulfonyloxybenzylamine has the structure:

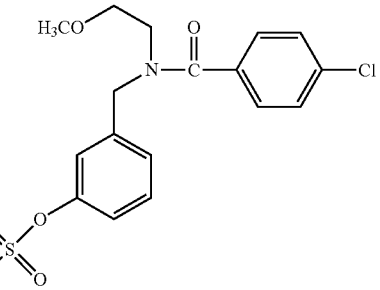

or a cosmetically acceptable salt thereof.

19. The method according to claim 16 wherein said N-substituted sulfonyloxybenzylamine has the structure of formula I:

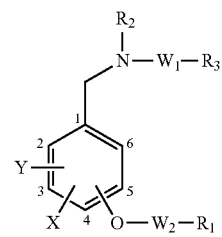

(I)

where:
$W_1$ and $W_2$ are independently CO, $CO_2$, CONH, $SO_2$ or $PO_3$;
$R_1$, $R_2$ and $R_3$ are independently $C_{1-20}$ hydrocarbons, each independently selected from alkyl, cycloalkyl, haloalkyl, alkoxyalkyl, heteroalkyl, heteroaryl, aryl, arylalkyl, alkylaryl, heteroaryl, heteroarylalkyl, and alkylheteroaryl, each being optionally substituted with C and/or 1-6 heteroatoms, including halogen, O, N and S;
X, Y each independently represent H or an optionally substituted alkyl, haloalkyl, alkoxy, amino, aminoalkyl, haloalkoxy, alkenyl, and where adjacent X, Y taken together can form a 5, 6, or 7 member ring;
and wherein the —O—$W_2$—$R_1$ group is attached to the phenyl ring at the 3- or 4-position.

* * * * *